(12) United States Patent
Yodfat et al.

(10) Patent No.: US 8,435,211 B2
(45) Date of Patent: May 7, 2013

(54) SYSTEMS, DEVICES AND METHODS FOR FLUID/DRUG DELIVERY

(75) Inventors: Ofer Yodfat, Maccabim-Reut (IL); Gavriel J. Iddan, Haifa (IL)

(73) Assignee: Medingo Ltd., Yoqneam Illit (IL)

( * ) Notice: Subject to any disclaimer, the term of this patent is extended or adjusted under 35 U.S.C. 154(b) by 527 days.

(21) Appl. No.: 11/989,681

(22) PCT Filed: Jul. 24, 2007

(86) PCT No.: PCT/IL2007/000932
§ 371 (c)(1),
(2), (4) Date: May 6, 2010

(87) PCT Pub. No.: WO2008/012817
PCT Pub. Date: Jan. 31, 2008

(65) Prior Publication Data
US 2010/0217230 A1    Aug. 26, 2010

Related U.S. Application Data

(60) Provisional application No. 60/833,110, filed on Jul. 24, 2006, provisional application No. 60/837,877, filed on Aug. 14, 2006.

(51) Int. Cl.
*A61M 31/00* (2006.01)
(52) U.S. Cl.
USPC .................................................. 604/93.01
(58) Field of Classification Search ............... 604/93.01, 604/164.12, 506
See application file for complete search history.

(56) References Cited

U.S. PATENT DOCUMENTS

| 4,886,499 A | 12/1989 | Cirelli et al. | |
| 5,429,810 A * | 7/1995 | Knaepler et al. | 422/300 |
| 5,848,990 A * | 12/1998 | Cirelli et al. | 604/136 |

(Continued)

FOREIGN PATENT DOCUMENTS

| EP | 0 272 530 B1 | 6/1988 |
| EP | 1 464 351 B1 | 10/2004 |
| EP | 1464351 A2 * | 10/2004 |
| WO | WO 2004/030726 A1 | 4/2004 |

OTHER PUBLICATIONS

Written Opinion of the International Searching Authority for PCT Application No. PCT/IL2007/000932.

(Continued)

*Primary Examiner* — Nicholas D. Lucchesi
*Assistant Examiner* — Diva K Chander
(74) *Attorney, Agent, or Firm* — Mintz Levin Cohn Ferris Glovsky and Popeo, P.C.

(57) ABSTRACT

Fluid delivery systems, methods and devices for delivering a therapeutic fluid to the body of the patient are disclosed. A fluid delivery device for delivering fluid to the body of the patient includes a housing having an upper wall, a lower wall and an opening. The device includes a well-arrangement mechanism disposed inside the housing. The well-arrangement mechanism includes a tubular member having a bore disposed between the wall openings. The device also includes a penetrating cartridge for delivery of therapeutic fluid to the body of the patient. The cartridge is configured to engage the bore following its insertion through the opening such that the therapeutic fluid can be delivered through the tubular member into the penetrating cartridge, and into the body of the patient when the penetrating cartridge engages the bore.

28 Claims, 14 Drawing Sheets

U.S. PATENT DOCUMENTS

| | | | |
|---|---|---|---|
| 6,093,172 A * | 7/2000 | Funderburk et al. | 604/135 |
| 6,423,035 B1 * | 7/2002 | Das et al. | 604/155 |
| 6,699,218 B2 * | 3/2004 | Flaherty et al. | 604/131 |
| 6,830,562 B2 * | 12/2004 | Mogensen et al. | 604/164.12 |
| 8,062,250 B2 * | 11/2011 | Mogensen et al. | 604/93.01 |
| 2008/0319414 A1 * | 12/2008 | Yodfat et al. | 604/506 |
| 2008/0319416 A1 * | 12/2008 | Yodfat et al. | 604/513 |
| 2010/0130932 A1 * | 5/2010 | Yodfat et al. | 604/151 |
| 2010/0217230 A1 * | 8/2010 | Yodfat et al. | 604/506 |
| 2011/0288390 A1 * | 11/2011 | Yodfat et al. | 600/365 |

OTHER PUBLICATIONS

International Search Report, PCT Application No. PCT/IL2007/000932, date of mailing Nov. 19, 2007.

* cited by examiner

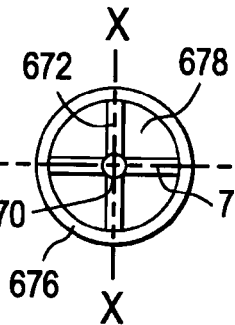
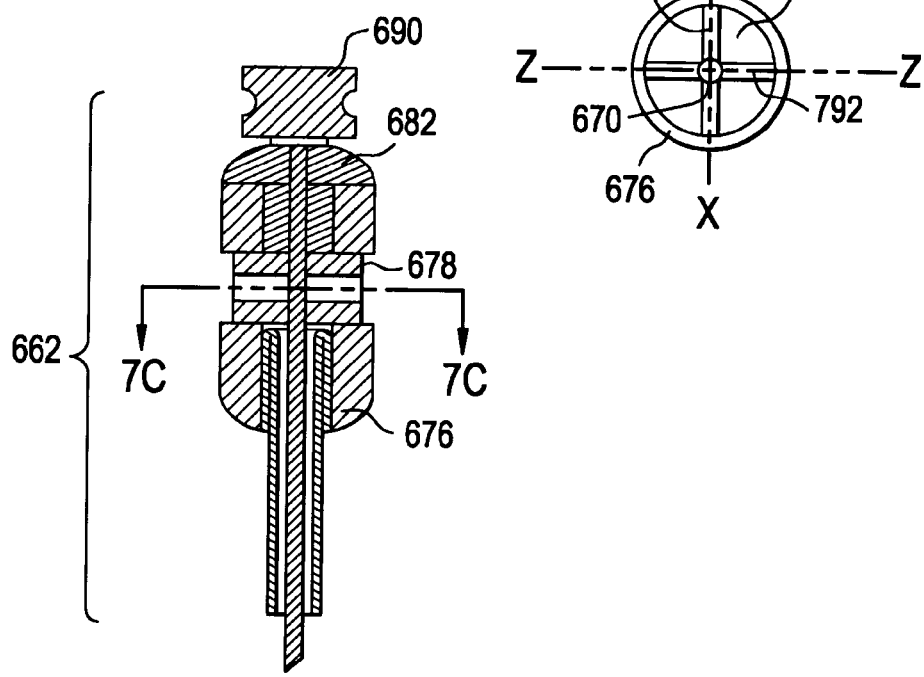
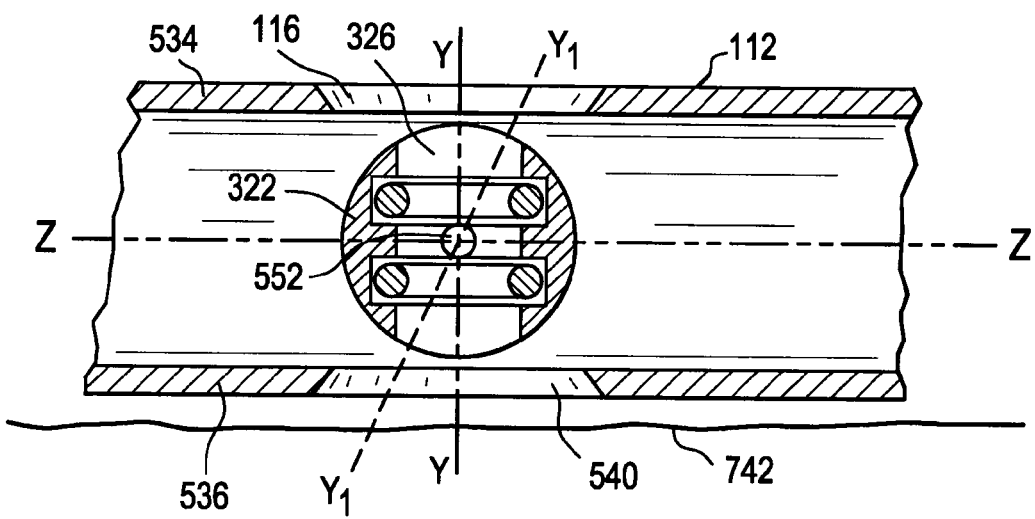

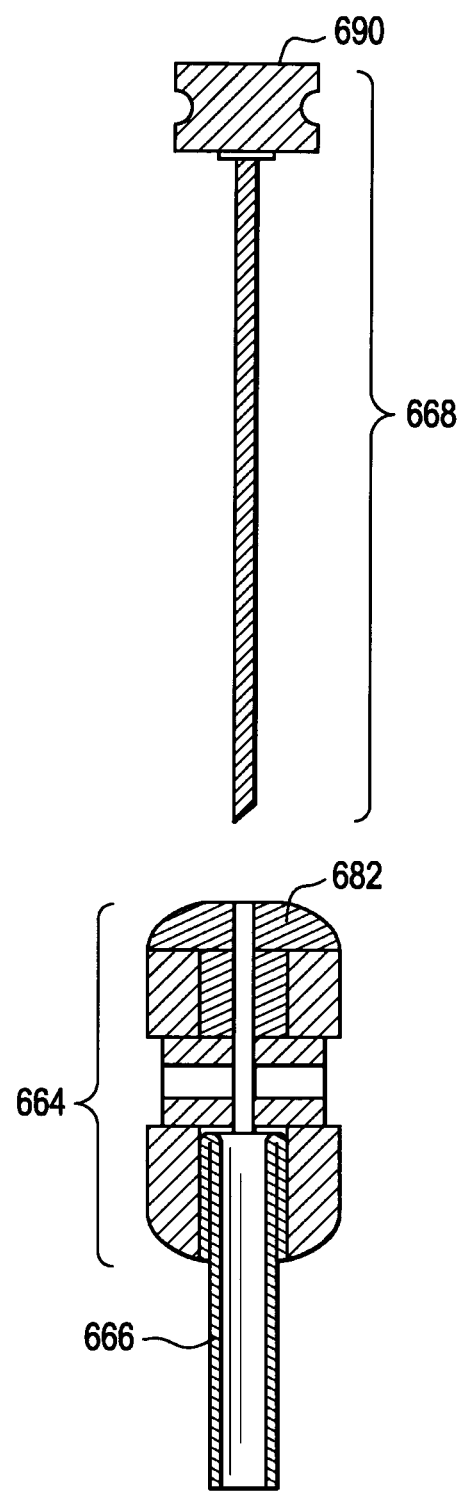

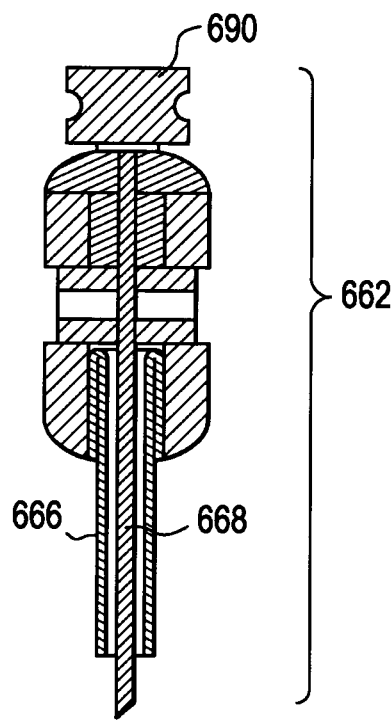
FIG. 9
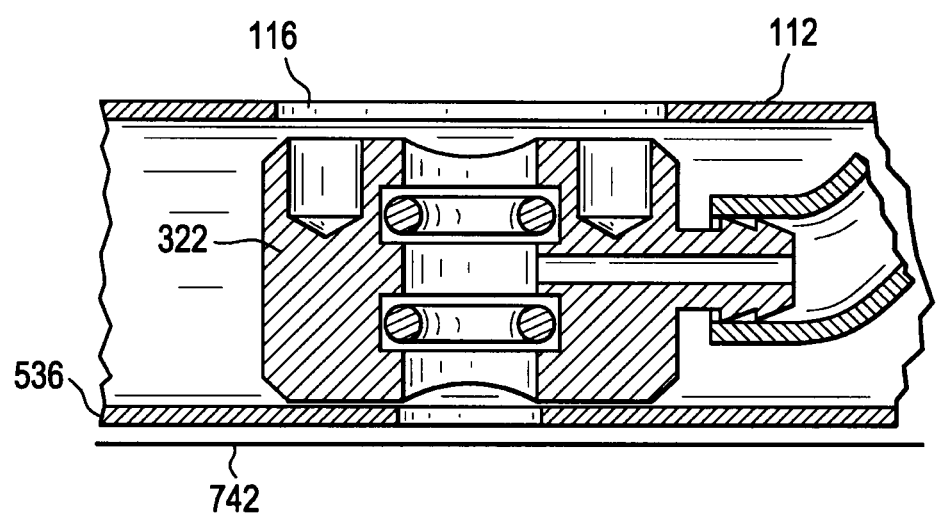

SYSTEMS, DEVICES AND METHODS FOR FLUID/DRUG DELIVERY

CROSS-REFERENCE TO RELATED APPLICATION

This application is a national stage entry of PCT/IL07/000,932, having an international filing date of Jul. 24, 2007, which claims priority to U.S. provisional patent application Nos. 60/833,110, filed Jul. 24, 2006 and 60/837,877, filed Aug. 14, 2006. Each of the foregoing disclosures is expressly incorporated herein in its entirety.

BACKGROUND OF THE INVENTION

1. Field of the Invention

The present invention relates to systems, devices and methods for delivering therapeutic fluids to a patient, and more particularly, to portable infusion devices (e.g., pumps). Some embodiments of the invention relate to infusion devices, which are adherable directly to a patient's skin. Some embodiments of the present invention are directed to a "well-arrangement", which couples a fluid delivery tube emerging from a reservoir in an infusion device to a cannula for subcutaneous insertion into the body of a patient.

2. Background of the Invention

Conventional subcutaneous delivery devices of therapeutic fluid into the body of a patient are also known as ambulatory "pager-like" portable infusion pumps that are used mainly for continuous insulin delivery. Typically, these pager-like pumps are attached to a belt which is secured to the patient. A long delivery tube is then connected to the reservoir within the device and also to a subcutaneous cannula of an infusion set.

Conventional ambulatory infusion pumps were developed for continuously delivering drugs to a patient. These ambulatory infusion pumps often contain a reservoir and a long tube for delivering the drug to a subcutaneous cannula of the infusion set. The cannula is often inserted together with a sharp penetrating member. Examples of such infusion pumps are disclosed in U.S. Pat. Nos. 6,423,035 and 8,872,200.

Additional examples of conventional fluid infusion devices are disclosed in the following patents. U.S. Pat. No. 6,093,172 to Funderburk et al. and U.S. Pat. No. 6,830,562 to Mogensen et al. disclose an injector device that includes a spring-loaded plunger for an automatic subcutaneous placement of an infusion set. U.S. Pat. No. 6,699,218 to Flaherty et al. discloses a skin-adherable device for delivering fluid to a patient that includes a housing with a reservoir chamber. The chamber is in fluid communication with a dispenser for dispensing the fluid from the reservoir in finite amounts to an exit port assembly from which liquid medication exits and enters the body of the patient. The device in the Flaherty patent also allows for an automatic cannula insertion. Such insertion is possible through the use of relatively heavy and bulky components which substantially extend device dimensions.

After insertion, the cannula is steadily retained in its subcutaneous location regardless of the movements of the body of the patient or relative movements between the housing of the pump and the cannula. This causes various difficulties with skin-adherable infusion devices.

Other problems with current infusion devices include reluctance of some patients to pierce their own skin with a needle. Such patients typically use automatic insertion devices to address this problem. Yet other patients prefer a manual insertion process.

Some disadvantages of conventional devices and methods for fluid delivery to a patient are summarized below:

Long tubing: in typical pager-like insulin pumps, the long fluid delivery tube tends to fold, kink, rupture and/or disconnect. Moreover, such tubes do not allow discreetness and restrict activity of the patient.

Rigid cannula connection: in conventional skin-adherable pumps, the cannula is rigidly connected to the housing, thus, abrupt movements of the body of the patient can cause patient discomfort, detachment of the cannula from the patient and/or its disconnection from the housing of the device.

Insertion mechanisms: some conventional insertion mechanisms are incorporated within the device housing. Such devices are relatively heavy and bulky and are carried by the user for the entire operating period (usually 3-4 days).

One length cannula: pre-mounted cannulas in some current infusion devices have only one predetermined length.

Fixed insertion angle: in some conventional pager-like devices, the patient can insert the infusion set only at a single predetermined penetration angle, usually 30°, 45° or 90°.

Thus, it is desirable to provide a system, device and/or method to address the above-noted problems of conventional fluid delivery devices. In particular, it is desirable to provide a subcutaneous cannula insertion that allows the patient maximal flexibility in choosing cannula length, insertion modes and penetration angles.

SUMMARY OF THE INVENTION

Some embodiments of the present invention relate to portable fluid delivery systems and devices as well as methods for delivering fluid to a patient. Such systems allow cannula insertion through a "well-arrangement" using a separate "inserter" that does not have to be carried after cannula insertion. The present invention further allows users to choose multiple cannula lengths and/or insertion angles.

In some embodiments of the present invention, the use of long tubing can be avoided by using a skin-adherable delivery device having a pump and a reservoir for therapeutic fluid, a delivery tube exiting the reservoir and a means for providing fluid communication between the tube and a cannula subcutaneously inserted into the patient. In some embodiments the means for providing fluid communication are referred to as a "well-arrangement".

Some embodiments of the present invention provide greater flexibility for the patient by allowing a desired penetration angle (for example, from about zero degrees to about 90 degrees (or greater)) to be selected by the patient. The present invention can be configured not limit patient movements and provide better safety for the patient by preventing disconnection of the infusion device from the cannula and interruption of supply of therapeutic fluid to the patient.

Some embodiments of the present invention allow:
Fluid communication between the delivery tube and the cannula by virtue of a dedicated well-arrangement;
Variation of penetration angle (e.g., 0 to 90 degrees (or greater));
Automatic and manual subcutaneous insertion of the cannula;
Relative displacement between the cannula and the pump so as to render the cannula insensitive to pump's housing movements.

In some embodiments, the delivery tube is brought in fluid communication with the cannula via a connecting element, referred to as a well-arrangement. This arrangement is discussed in a co-pending, co-owned Israel patent application No. 171813, disclosure of which is incorporated herein by reference in its entirety. The well-arrangement allows insertion of a needle assembly that includes a penetrating member (e.g., a needle) and cannula. After piercing the skin, followed by inserting the cannula and evacuating the needle, a fluid communication between the delivery tube, the cannula and the subcutaneous tissue is established and maintained.

In some embodiments, the well arrangement can include an opening/bore on its upper side that can be configured for priming. The patient can fill the reservoir and the delivery tube. By observing drops of fluid in the opening/bore, the patient becomes aware that no air bubbles are left in the system. After piercing the skin of the patient, the opening/bore can be configured to be sealed by a rubber cap. The rubber cap can be attached to the cannula to prevent leakage during operation of the device. The lower side of the well can be configured to be closed by a rubber septum. During piercing of the skin, the lower rubber septum is pierced by the needle, while the rubber cap seals the upper opening/bore. Using the well-arrangement mechanism, the present invention can also be configured to connect the fluid delivery tube and the cannula.

In some embodiments, the well-arrangement can be configured to be connected to the housing of a fluid delivery device in a floating arrangement. In particular, using this arrangement, relative displacement between the cannula and the housing can be permitted, thereby, reducing undesirable patient discomfort and/or eliminating a possibility for cannula disconnections.

In some embodiments, the well-arrangement includes a tubular member, which can be provided with a transversal passage for insertion of a cannula. The transversal passage can be configured to be in fluid communication with the delivery tube through a longitudinal lateral passage provided in the tubular member. That region of the housing, which receives the well can be configured and/or dimensioned to permit forcible rotation of the tubular member along its longitudinal axis. By virtue of this provision, one can vary an inclination of the transversal passage with respect to the patient's skin, and thus, the angle at which the penetrating member pierces the skin and the cannula is inserted can be varied. A penetrating assembly can be configured to be inserted in the tubular member either manually or automatically by means of a dedicated tool (e.g., an "inserter", one such inserter is described below). The tubular member could be "floating" as described above.

In some embodiments, a fluid delivery device for delivering a therapeutic fluid to the body of a patient is provided and can be configured to include a patch unit having a disposable part and a reusable part. The disposable part can be configured to include a well-arrangement provided between a first wall and a second wall of the disposable portion. A first aperture can be provided in the first wall and a second aperture can be provided in the second wall. The well-arrangement can include a tubular member having a bore, an inlet port in fluid communication with a delivery tube, and a lateral channel between the inlet port and the bore.

In the above embodiments, the tubular member can be configured to be rotatable, such that the bore can be positioned in a plurality of positions.

Some embodiments of the present invention include a penetrating cartridge for use in a fluid delivery device. The penetrating cartridge can be configured to include a body portion, a cannula and a penetrating member adapted to pierce the skin of a patient. The body portion includes a first lumen for receiving fluid, and a second lumen in communication with the cannula and the first lumen.

In yet other embodiments, a fluid delivery system for delivering a therapeutic fluid to the body of a patient can be configured to include a fluid delivery device having a patch unit including a disposable part and a reusable part. The disposable part includes a first wall having a first aperture, a second wall having a second aperture, a fluid delivery tube and a well-arrangement provided between the first wall and the second wall. The well-arrangement can include a tubular member having a bore, an inlet port in fluid communication with the delivery tube and a lateral channel between the inlet port and the bore. The tubular member can be rotatable, such that the bore can be positioned in a plurality of positions relative to vertical (for example) with respect to the first and/or second wall of the disposable portion. The system can also include a penetrating cartridge receivable in the bore of the tubular member, where the penetrating cartridge may include a cannula and a penetrating member adapted to pierce the skin of a patient. The body portion of the penetrating cartridge can include a first lumen for receiving fluid and a second lumen in communication with the cannula and the first lumen.

An "inserter" tool can be included in some embodiments of the invention, as a means for automatic insertion of the penetrating assembly ("penetrating cartridge") in the tubular member. The inserter tool can be preloaded with the penetrating cartridge either by the patient or by the manufacturer before insertion. The user can align the inserter tool with the transverse passage and release the preloaded penetrating cartridge by pushing a button of an actuator.

The tubular member and the inserter tool can be provided with respective indentation grooves and protrusions to allow convenient engagement of the inserter tool with the tubular member and accurate alignment of the penetrating member with the transversal passage.

In some embodiments, the inserter has an additional function. Upon engagement of the inserter with the indentation groves of the tubular member, the user can rotate the tubular member (containing the well) to the desired penetrating angle. In other words, the inserter is not just used for alignment, it may also be used as a means for adjusting the penetrating angle.

In some embodiments, the present invention relates to a fluid delivery device for delivering fluid to the body of the patient. The fluid delivery device includes a housing having an upper wall and a lower wall, wherein the upper wall includes an upper opening and the lower wall includes a lower opening, a well-arrangement mechanism configured to be disposed inside the housing and between the upper wall and the lower wall and including a tubular member having a bore, wherein the bore is configured to be disposed between the upper opening and the lower opening, and a penetrating cartridge for delivery of therapeutic fluid to the body of the patient, wherein the penetrating cartridge is configured to engage the bore following its insertion through the upper opening and the lower opening. Therapeutic fluid is configured to be delivered through the tubular member into the penetrating cartridge into the body of the patient when the penetrating cartridge engages the bore.

In some embodiments, the present invention relates to a method for delivery fluid to the body of the patient using a fluid delivery device. The fluid delivery device includes a housing having an upper wall and a lower wall, wherein the upper wall includes an upper opening and the lower wall includes a lower opening, a well-arrangement mechanism configured to be disposed inside the housing and between the upper wall and the lower wall and including a tubular member having a bore, wherein the bore is configured to be disposed between the upper opening and the lower opening, and a penetrating cartridge for delivery of therapeutic fluid to the body of the patient, wherein the penetrating cartridge is configured to engage the bore following its insertion through the upper opening and the lower opening. The method includes the steps of inserting the penetrating cartridge into the bore of the well-arrangement mechanism until the penetrating cartridge engages the bore, and when the penetrating cartridge engages the bore, delivering therapeutic fluid through the tubular member into the penetrating cartridge into the body of the patient.

Further features and advantages of the invention, as well as structure and operation of various embodiments of the invention, are disclosed in detail below with references to the accompanying drawings.

BRIEF DESCRIPTION OF THE FIGURES

The present invention is described with reference to the accompanying drawings. In the drawings, like reference numbers indicate identical or functionally similar elements. Additionally, in most cases, the left-most digit(s) of a reference number identifies the drawing in which the reference number first appears.

FIG. 7A is another view of the penetrating cartridge shown in FIG. 6.

FIG. 7B is a cross-sectional view of an exemplary barrel of the well-arrangement mechanism, according to some embodiments of the present invention.

FIG. 7C is a cross-sectional view of the penetrating cartridge shown in FIG. 6.

FIG. 8 is an exploded view of the penetrating cartridge shown in FIG. 6.

FIG. 9 is an exploded view of the barrel shown in FIG. 7B and the penetrating cartridge shown in FIG. 6.

DETAILED DESCRIPTION OF THE INVENTION

Figure 1:
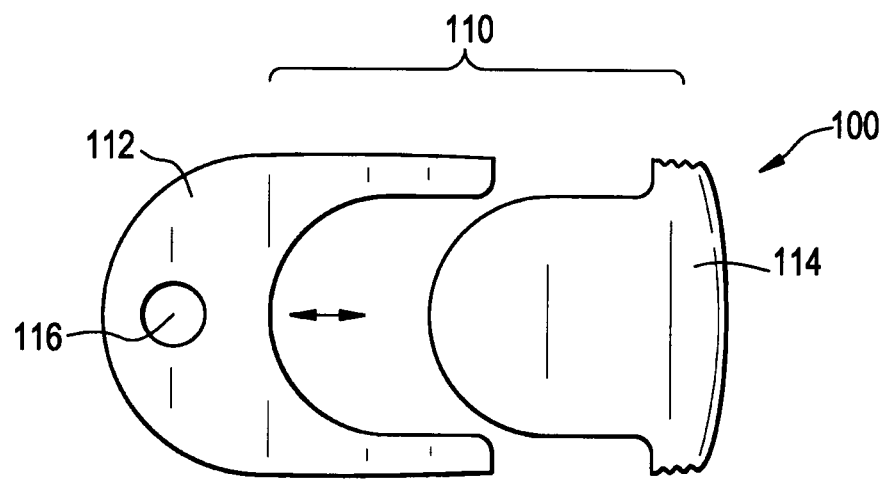
FIG. 1 is an exploded view of an exemplary fluid delivery device, according to some embodiments of the present invention.

FIG. 1 illustrates an exploded view of an exemplary fluid delivery device 100, according to some embodiments of the present invention. The fluid delivery device 100 includes a patch unit 110 configured to be adherable to the body of the patient and a remote control unit (not shown in FIG. 1). The patch unit 110 includes a disposable part 112, which may be detachably connected to a reusable part 114. Some embodiments of the fluid delivery device having a patch unit are disclosed in the co-owned, co-pending Israel patent application No. 171813, the disclosure of which is incorporated herein by reference in its entirety. One of the advantages of the above configuration is that the relatively expensive components of the fluid delivery device can be deployed in the reusable part and the less expensive components can be deployed in the disposable part. As such, this device is more cost-effective in manufacture, sale, and use.

Figure 2:
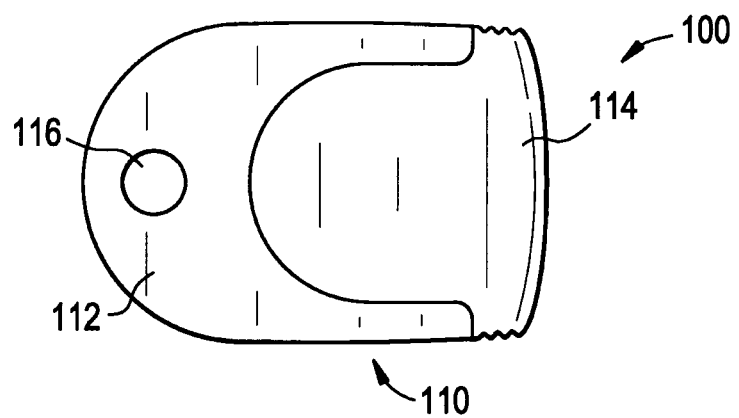
FIG. 2 is an assembled view of the exemplary fluid delivery device shown in FIG. 1.

FIG. 2 illustrates an assembled view of the exemplary patch unit 110 of the fluid delivery device 100 shown in FIG. 1, according to some embodiments of the present invention. As shown in FIG. 2, the reusable part 114 is configured to be connected with the disposable part 112. The disposable part 112 includes an upper aperture 116. The upper aperture 116 is configured to provide access to a tubular member of a well-arrangement mechanism (not shown in FIG. 2). The well-arrangement mechanism is configured to be disposed between upper wall and lower wall (not shown in FIG. 2, but are discussed below in connection with FIG. 5) of the disposable part 112.

Figure 3:
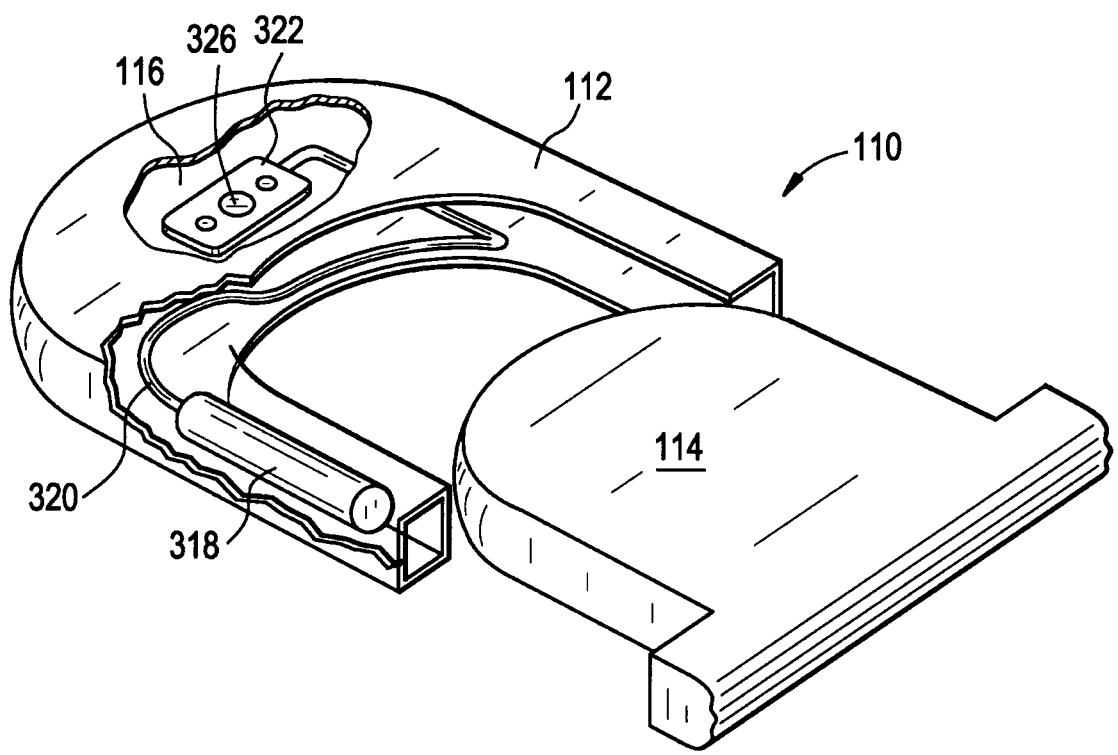
FIG. 3 is another exploded view of an exemplary fluid delivery device shown in FIG. 1.
Figure 4:
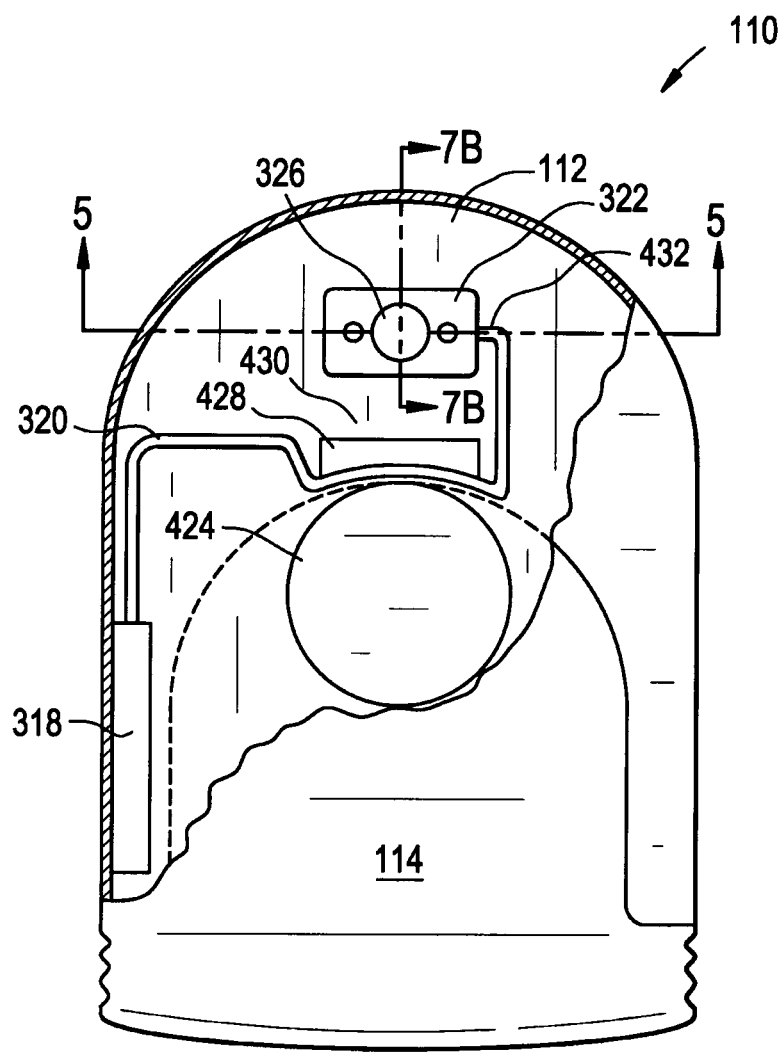
FIG. 4 is another assembled view illustrating additional detail of the fluid delivery device shown in FIG. 1.

FIGS. 3 and 4 illustrate additional detail, including components that reside within the reusable part 114 and the disposable part 112, of the patch unit 110 shown in FIGS. 1 and 2. The patch unit 110 includes a reservoir 318 filled with a therapeutic fluid, a delivery tube 320 and a tubular member 322 of the well-arrangement mechanism provided with a bore 326. The delivery tube 320 is configured to connect the reservoir 318 and the tubular member 322, so that they are in fluid communication with each other. The patch unit 110 can be configured to include a pump for dispensing the therapeutic fluid from the reservoir 318 to a cannula (not shown in FIG. 3, but is discussed below in connection with FIG. 6), which can be configured to be inserted subcutaneously into the body of the patient. In some embodiments, the cannula can be configured to be inserted into the tubular member 322 and further configured to enter subcutaneously into the body of the patient through the bore 326 and through an appropriate lower aperture (not shown in FIGS. 3 and 4, but is discussed in connection with FIG. 5 below) that can be disposed in the lower wall of the disposable part 112.

Referring to FIG. 4, the delivery tube 320 can be configured to be placed between a stator plate 428 and rollers of a rotating wheel 424 of the pump. The rollers are not seen in FIG. 4. of the pump. The pump can be a peristaltic pump or any other suitable pumping mechanism. In some embodiments, to make the patch unit 110 operational, the stator plate 428 can be pressed using a spring 430 towards the rollers. This way, when the wheel is rotating, the rollers press the delivery tube 320 to the stator plate 428 thereby squeezing the delivery tube 320, which can be referred to as a positive displacement movement. Thus, the fluid is periodically pumped from the reservoir 318 into the delivery tube 320 and further into the cannula that is subcutaneously inserted in the body of the patient (not shown in FIG. 4). In some embodiments of the present invention, the disposable part 112 is configured to accommodate a well-arrangement mechanism, which is described further. The well-arrangement mechanism can be configured to be situated between an outlet port 432 of the delivery tube 320 and the cannula. Because of the well-arrangement mechanism, the delivery tube 320 may be brought in fluid communication with the cannula and allow supply of the therapeutic fluid from the reservoir 318 to the body of the patient.

FIG. 4 also illustrates cross-sectional lines 5-5 and 7B-7B, which are drawn across the tubular member 322. The details of the respective cross-sections 5-5 and 7B-7B of the patch unit 110 are illustrated in FIGS. 5 and 7A-C, respectively.

Figure 5:
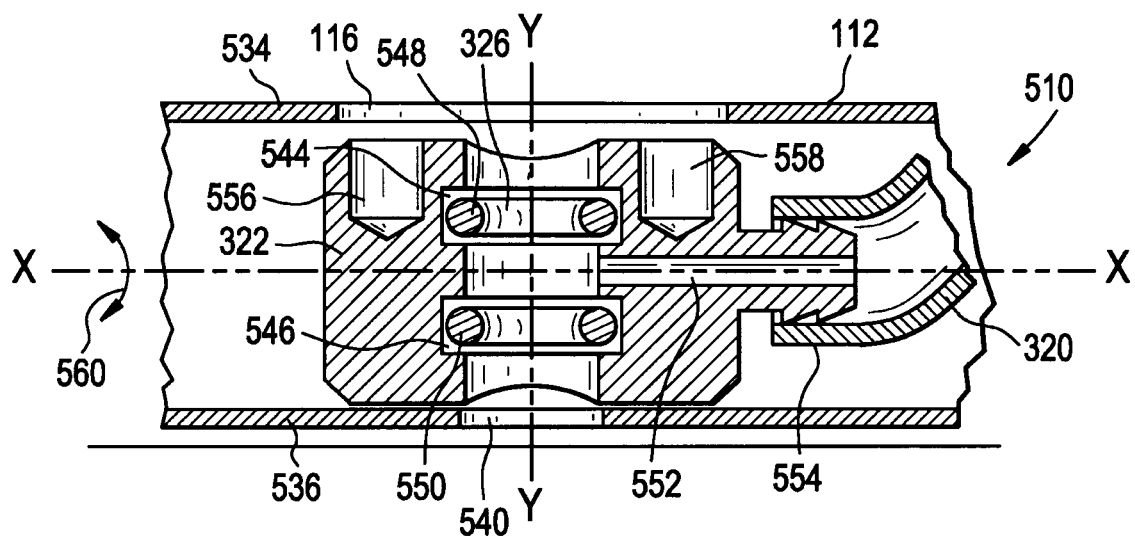
FIG. 5 illustrates an exemplary well-arrangement mechanism of a fluid delivery device, according to some embodiments of the present invention.

FIG. 5 illustrates an exemplary well-arrangement mechanism 510 as shown by a cross-sectional view of the patch unit 110 taken along line 5-5 (shown in FIG. 4), according to some embodiments of the present invention. The well-arrangement mechanism 510 includes the tubular member 322 accommodated in a space provided in the disposable part 112 between an upper wall 534 and a lower wall 536 thereof. In some embodiments, the tubular member 322 can be configured as a barrel that is defined by a cylindrical periphery wall and by two opposite butt ends. For ease of description only, the tubular member 322 will be referred to as the barrel 322. The barrel 322 has a longitudinally directed central X-axis. The bore 326 extends in the barrel 322 along central Y-axis and perpendicularly to X-axis, as shown in FIG. 5. The bore 326 can be configured to be accessible through the aperture 116 in the upper wall 534. The lower wall 536 of the disposable part 112 includes an aperture 540 that corresponds to the aperture 116. The aperture 540 is located opposite the aperture 116 and the combination of apertures 116 and 540 is configured to provide an access to the skin of the patient through the barrel 322 in the well-arrangement mechanism 510. The sizes and shapes of the apertures 116 and 540 can be configured to accommodate insertion of the cannula and a penetrating member (discussed below) into the body of the patient at any desired angle and/or position.

The well-arrangement mechanism 510 further includes two annular grooves 544, 546 and corresponding sealing rings 548, 550, which are configured to be placed inside the annular grooves 544, 546, respectively. The barrel 322 of the well-arrangement mechanism 510 further includes a lateral channel 552 configured to extend along the X-axis from the bore 326 toward the delivery tube 320. The lateral channel is provided with an inlet port 554, which is disposed at the point where the delivery tube 320 connects to the barrel 322. The lateral channel 552 is further configured to provide fluid communication between the bore 326 and the inlet port 554. Since delivery tube 320 is connected to the inlet port 554, therapeutic fluid can be delivered from the reservoir 318 through the bore 326 to the body of the patient. The barrel 322 further includes two indentation grooves 556 and 558, which can be disposed on the cylindrical peripheral wall of the barrel 322 (the grooves 556 and 558 will be discussed in more detail below in connection with FIGS. 16-23).

In some embodiments, the size of the barrel 322 and its disposition between the upper wall 534 and the lower wall 536 allow rotational motions of the barrel 322 around its X-axis, as shown by a directional arrow 560. As the barrel 322 is rotated around the X-axis, the orientation of the Y-axis changes and, thus, the bore 326 rotates along with the barrel 322 and becomes inclined with regard the skin of the patient (assuming that prior to rotation, the Y-axis is substantially perpendicular to the skin of the patient or any other reference surface). As can be understood by one skilled in the art, the barrel 322 can be rotated to any desired angle. This allows the cannula to be inserted through the bore 326 in the skin of the patient at any desired penetration angle.

The barrel 322 can be manufactured from an inexpensive material (e.g., plastic, polyethylene, or any other suitable material) that can be designed to be compatible with insulin or any other therapeutic fluid and can be also configured to be disposable along with the disposable part 112 of the patch unit 110 after each use of the fluid delivery device 100.

Figure 6:
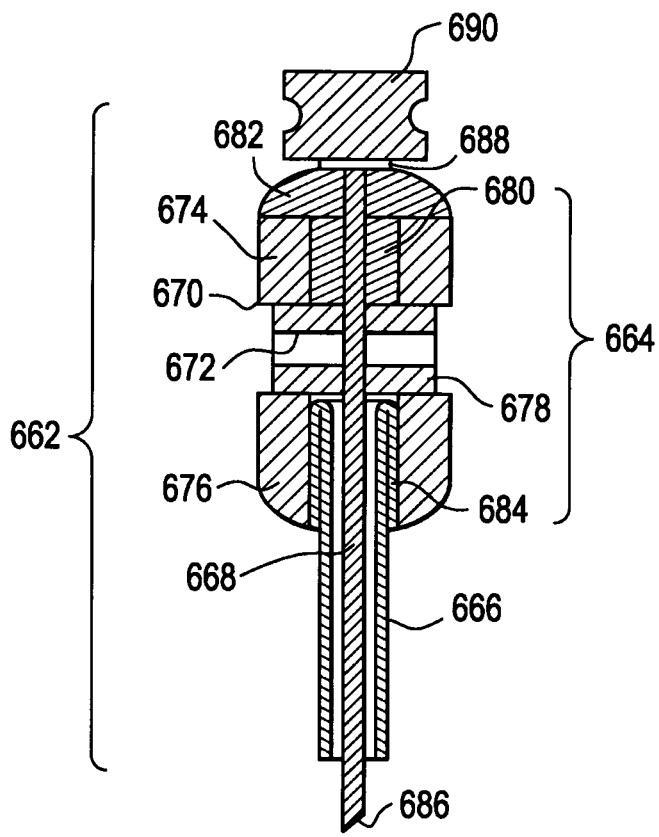
FIG. 6 illustrates an exemplary penetrating cartridge of the well-arrangement mechanism shown in FIG. 5, according to some embodiments of the present invention.

FIG. 6 illustrates a penetrating cartridge 662 that is configured to be inserted into the barrel 322 and, in particular, into the bore 326. The penetrating cartridge 662 is configured to be disposable and can be disposed off along with the disposable part 112. The penetrating cartridge 662 is configured to be inserted into the barrel 322 along the Y-axis, which is shown in FIG. 5.

In some embodiments, the penetrating cartridge 662 includes a body portion 664, a cannula 666 connected to the body portion 664, and a penetrating member 668 having a tip 686, which is adapted to pierce the skin of the patient. The body portion 664 can be configured to include a long lumen 670 and a short lumen 672. The long lumen 670 can be configured to extend longitudinally along the body portion 664. The short lumen 672 can be configured to extend transversely across the body portion 664. The penetrating member 668 can be inserted in the body portion 664 and removed therefrom through the long lumen 670.

The body portion 664 further includes an upper region 674, a lower region 676 and an intermediate region 678. The upper region 674 and the lower region 676 can be configured to have the same outside diameter, while the intermediate region 678 can be configured to have a smaller diameter than outer diameter of the upper and lower regions 674, 676. The short lumen 672 can be configured to extend along the intermediate region 678. The short lumen 672 can be configured to be perpendicular to the long lumen 670 and can be further configured to be in fluid communication with the short lumen 672. In some embodiments of the present invention, the short lumen 672 can be configured to be parallel to the X-axis of the barrel 322, which is shown in FIG. 5.

The upper region 674 can be configured to accommodate an elastic sealing plug 680 that can be used to seal the long lumen 670 when the penetrating member 668 is not inserted in the body portion 664. The upper region 674 can be configured to be closed by a cover 682. The cover 682 can include a hole for insertion the penetrating member 668. Once the penetrating member 668 is inserted through the cover 682, the penetrating member 668 pierces the plug 680, which elastically seals the interior of the body portion 664. In some embodiments, the lower region 676 is configured to include a sealing bushing 684 that seals the cannula 666 and the long lumen 674. The penetrating member 668 can be configured as a needle provided with a sharp tip or end 686 that is suitable for penetrating the skin of the patient. The needle can also includes a blunt end 688 having a head 690 that is opposite of the tip 686. The head 690 is configured to be gripped by the patient when the penetrating member 668 is being inserted in the body portion 664 or removed therefrom.

The outside diameter of the upper and lower regions 674, 676 can be selected in such a manner, that sealing rings 548, 550 in the barrel 322 seal the body portion 664 when the penetrating cartridge 662 is inserted in the bore 326. Furthermore, the body portion 664 can be configured to be dimensioned in such a manner that upon insertion of the penetrating cartridge 662 into the barrel 322, the short lumen 672 can be configured to be aligned with lateral channel 552 of the barrel 322.

FIGS. 7A and 7B are cross-sectional views of the penetrating cartridge 662 and the barrel 322, respectively. FIG. 7B is a cross-sectional view of the barrel 322 taken along cross-sectional direction 7B-7B shown in FIG. 4. FIG. 7B further illustrates the barrel 322 in a rotated position, where the barrel has been rotated around X-axis (not shown in FIG. 7B, but shown in FIG. 5; in FIG. 7B, the X-axis is Y-axis and Z-axis, thus, it is perpendicular to the face of the page). FIG. 7B also illustrates barrel's Y-axis being perpendicular to the upper wall 534 and the lower wall 536. Once the barrel 322 is rotated (whether forcibly or without application of force), the bore 326 becomes tilted, as shown in FIG. 7B, and, thus, the direction of the Y-axis alters. The new direction of the Y-axis is shown by the dotted line $Y_1$-$Y_1$. The line $Y_1$-$Y_1$ designates an angle at which the penetrating member 668 approaches the skin of the patient and at which the cannula 666 is inserted in the skin 742.

FIG. 7A also includes a cross-sectional line 7C-7C that is drawn across the intermediate region 678 of the penetrating cartridge 662. FIG. 7C is a cross-sectional view of the cartridge 662 taken along line 7C-7C. As can be seen from FIG. 7C, the intermediate region 678 of the penetrating cartridge 662 further includes an auxiliary short lumen 792. The auxiliary short lumen 792 can be configured to be perpendicular to the short lumen 672 and can be further configured to be in fluid communication with the long lumen 670. Thus, the short lumen 672 and the auxiliary short lumen 792 are respectively directed along X-axis and Z-axis, which is perpendicular to the X-axis shown in FIGS. 5 and 7B. As can be understood by one skilled in the art, additional short lumens and/or auxiliary short lumens can be provided in the penetrating cartridge 662 for the purposes of establishing fluid communication with the long lumen 670.

FIGS. 8-11 illustrate various views of components of the fluid delivery device 100 at various stages. FIG. 8 illustrates an exploded view of the penetrating cartridge 662, according to some embodiments of the present invention. As shown in FIG. 8, the penetrating member 668 is removed from the body portion 664 (i.e., not yet inserted into the cannula 666). Thus, prior to being used by the patient (or a medical professional), the penetrating member 668 is configured to be inserted in the body portion 664 of the penetrating cartridge 662 through a hole in the cover 682. As can be understood by one skilled in the art, the penetrating member 662 can be configured to be inserted by the patient, doctor, or any other medical professional, or by the manufacturer of the penetrating cartridge 662. Further, the penetrating cartridge 662 can be made from an inexpensive material, such as plastic, polyethylene, or any other suitable material. This way the penetrating cartridge 662 can be disposed after each use of the fluid delivery device 100.

Figure 10:
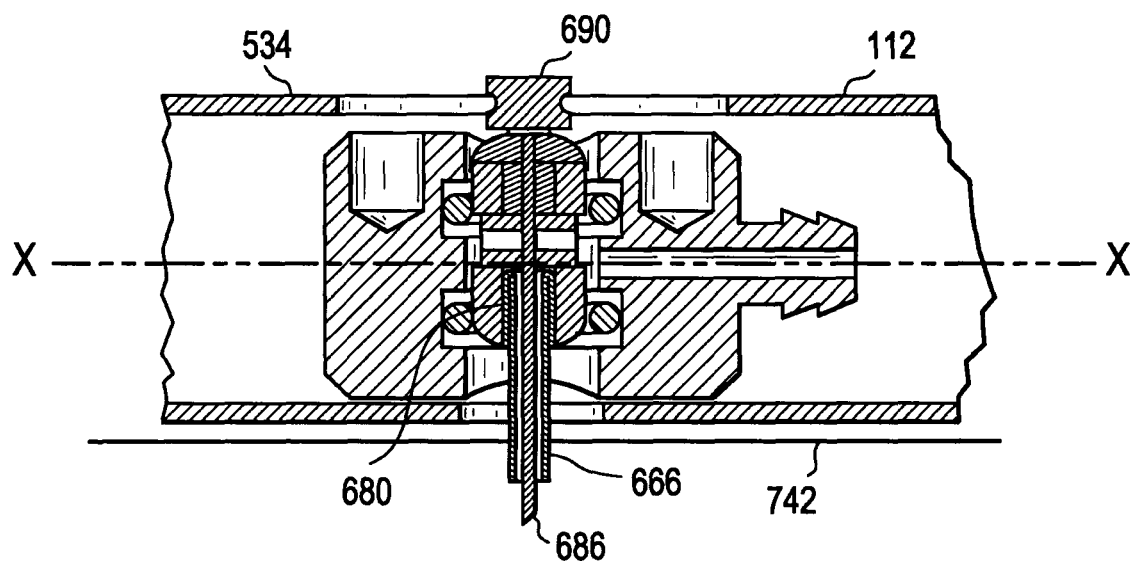
FIG. 10 is a cross-sectional view of the penetrating cartridge being inserted into the barrel, according to some embodiments of the present invention.

FIG. 9 illustrates an assembled view of the penetrating cartridge 662, having the penetrating member 668 inserted into the body portion 664, placed above the outer aperture 116 for insertion of the penetrating cartridge 662 into the bore 326. As shown in FIG. 9, the lower wall 536 of the disposable part 112 is configured to be placed adjacent the skin 742 of the patient. FIG. 10 illustrates the penetrating cartridge 662 being inserted into the bore 326 of the barrel 322. As shown in FIG. 10, the penetrating member 668 is inserted in the downward direction along the body portion 664. When the penetrating member 668 is inserted into the bore 326, the cannula 666 along with its sharp end 686 is configured protrude from the opening 540 in the lower wall 536 and to pierce the skin 742 of the patient. In some embodiments (as shown in FIG. 10), the head 690 of the penetrating member 668 is configured to remain above the upper wall 534 of the disposable part 112 and, thus, it is can be gripped by the patient for the purposes of removal of the penetrating member 668 from the body of the patient. As further shown in FIG. 10, the penetrating member 668 is configured to be perpendicular to the skin 742 of the patient. As can be understood by one skilled in the art, if the barrel 322 is rotated around the X-axis (shown in FIG. 5), the angle of penetration of the skin 742 by the penetrating member 668 will change accordingly.

Figure 11:
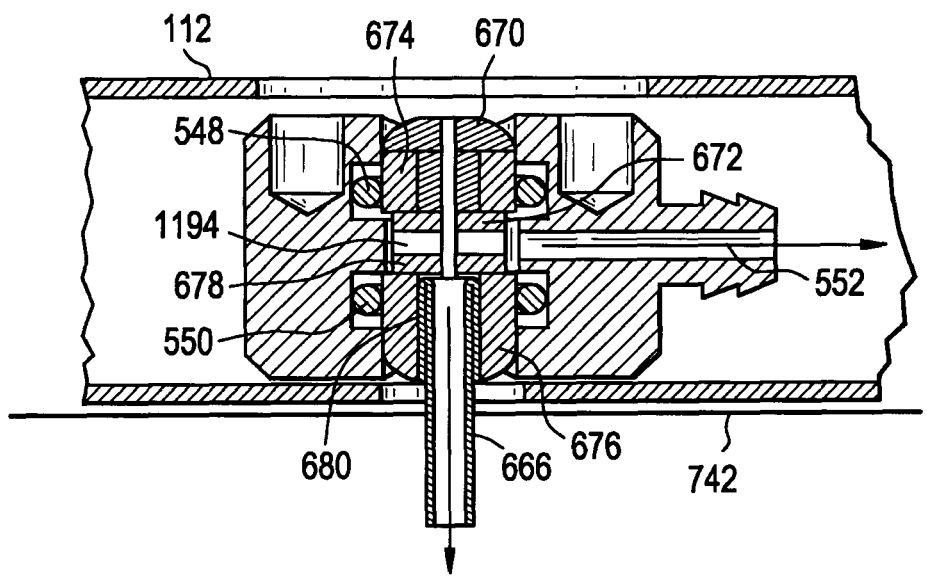
FIG. 11 is a cross-sectional view of the penetrating cartridge being inserted into the barrel and having a penetrating member removed from the penetrating cartridge, according to some embodiments of the present invention.

FIG. 11 illustrates the penetrating cartridge 662 having the penetrating member 668 removed from the penetrating cartridge 662 while the cannula 666 remains inserted into the skin 742. In some embodiments, to remove the penetrating member 668 from the skin 742, the patient (or any other medical professional) can grip the head 690 and pull it in an upward direction away from the skin 742. Upon removal the penetrating member 668, the interior of the penetrating cartridge 668 continues to remain sealed from the exterior (and thereby from effects of the outside elements). This is due to the presence of the resilient sealing plug 680.

In some embodiments, because the diameter of the intermediate region 678 is configured to be less than the diameters of the upper region 674 and of the lower region 676, an annular space 1194 can be provided between the barrel 322 and the intermediate region 678 of the penetrating cartridge 662. This annular space 1194 can be configured to be sealed by the sealing rings 548, 550. The annular space 1194 is further configured to be filled with therapeutic fluid that is configured to enter the annular space 1194 through the lateral channel 552. The pump can be configured to fill the annular space 1194 with therapeutic fluid. The annular space 1194 can be filled manual, automatically, periodically, or at any desired time interval. As illustrated in FIG. 11, the annular space 1194 is configured to be in fluid communication with long lumen 670. Such fluid communication is accomplished via short lumens 672, 792 (not shown in FIG. 11). Thus, by flowing from the annular space 1194 into the long lumen 670, therapeutic fluid enters the cannula 666.

Figure 12:
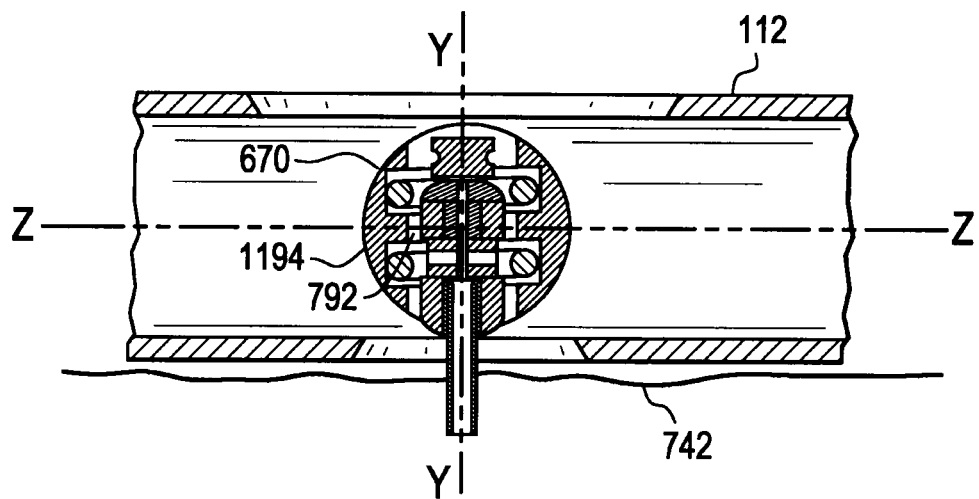
FIG. 12 is yet another cross-sectional view of the penetrating cartridge being inserted into the barrel and having a penetrating member removed.

FIG. 12 is another cross-sectional view of the penetrating cartridge 662 taken along 7B-7B (as shown in FIG. 4 above). The penetrating cartridge 662 is illustrated subsequent to its insertion into the barrel 322. The annular space 1194 is illustrated as being in fluid communication with the long lumen 670 via the short lumen 792.

Figure 13:
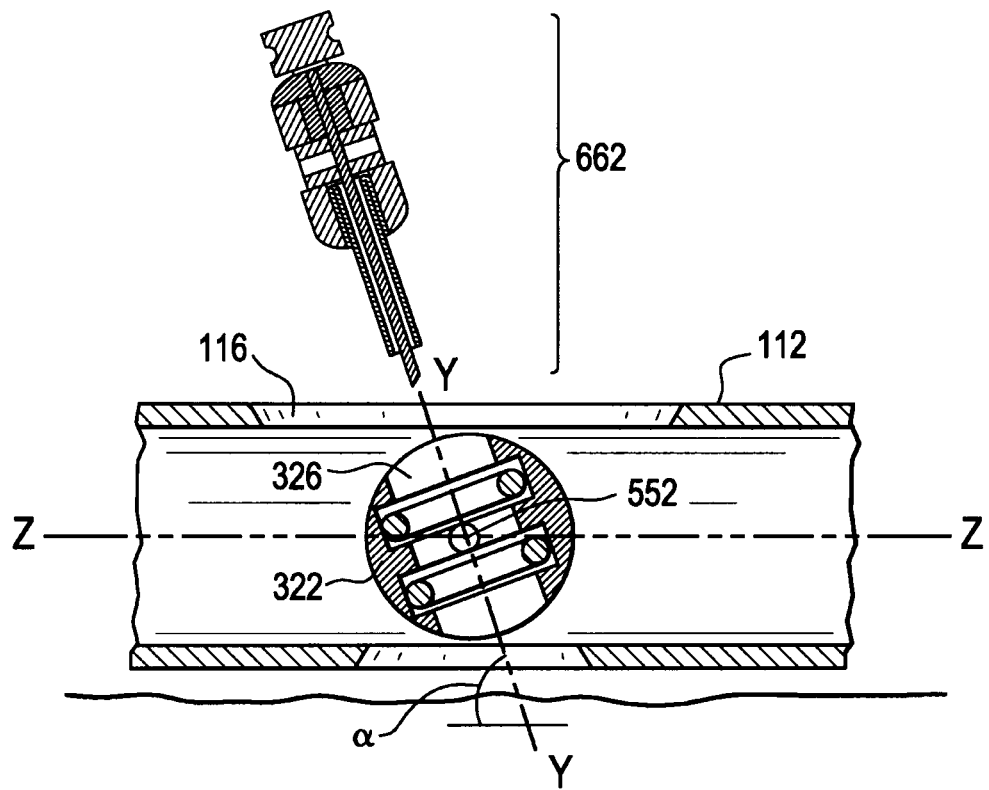
FIG. 13 is a cross-sectional view of a tilted penetrating cartridge prior to insertion into the barrel of the well arrangement mechanism, according to some embodiments of the present invention.

FIG. 13 is yet another illustration of the penetrating cartridge 662 being placed near the opening 116 in the upper wall 534 of the disposable part 112 for insertion into the bore 326 at an angle α. The angle α is formed by rotating the barrel 322 around the X-axis of the barrel and is angular displacement of the Y-axis, which runs longitudinally across the bore 326, with respect to surface the skin 742 of the patient. In order to insert the penetrating cartridge 662 into the bore 326, the penetrating cartridge 662 is also tilted at the same angle α to align with the bore 326. An example of the rotation of the barrel 322 and tilting of the penetrating cartridge 662 is discussed below with regard to FIGS. 16-18.

Figure 14A:
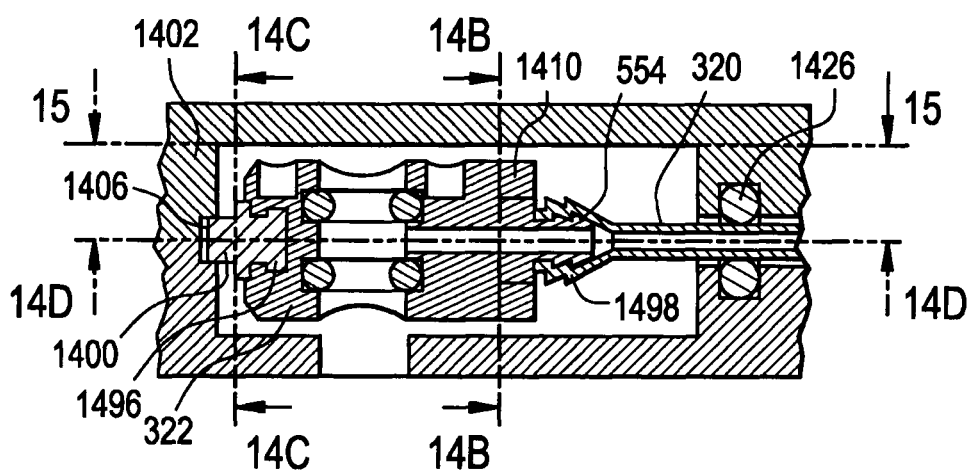
FIG. 14A-D are various cross-sectional views of the barrel of the well-arrangement mechanism, according to some embodiments of the present invention.
Figure 14B:
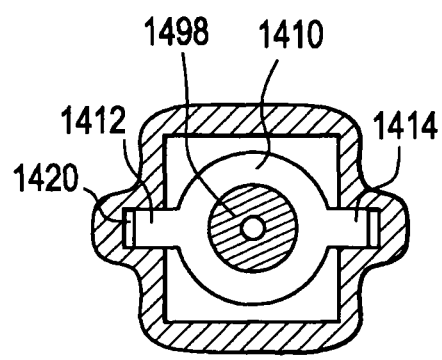
Figure 14C:
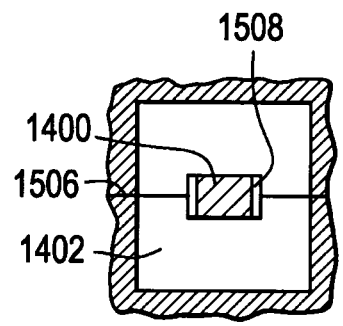
Figure 14D:
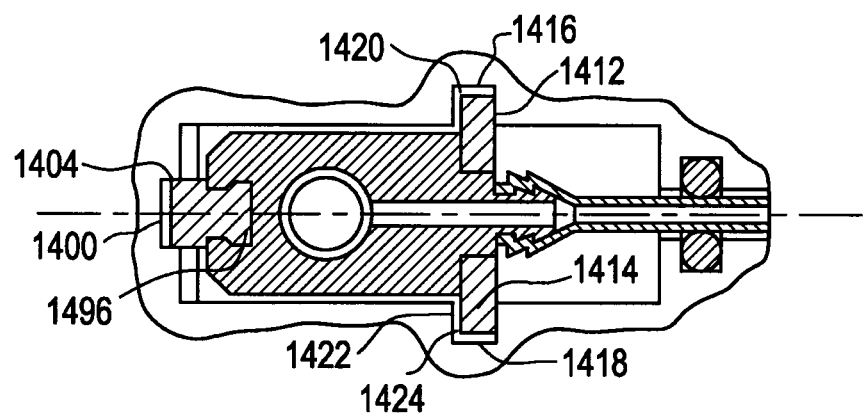
Figure 15:
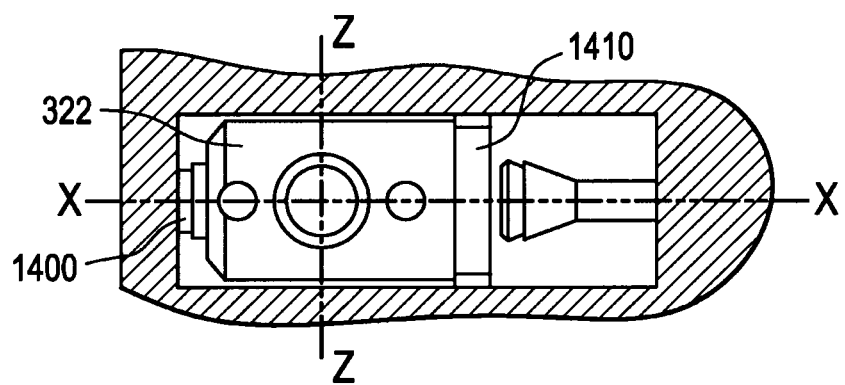
FIG. 15 is yet another cross-sectional view of the barrel shown in FIGS. 14A-D.

FIGS. 14-15 illustrate an exemplary embodiment of the "floating" feature of the well-arrangement mechanism. In some embodiments of the present invention, the term "floating" means that the barrel 322 can be configured to be relatively displaceable with respect to the upper wall 534 and the lower wall 536 of the disposable part 112. In some embodiments, a gap is provided between the barrel 322 and vertical walls of the disposable part 112, which are adjacent to the barrel.

FIGS. 14A-D illustrate cross-sectional views of the barrel 322. Specifically, FIG. 14B is a cross-sectional view of the barrel 322 taken at line B-B shown in FIG. 14A. FIG. 14C is a cross-sectional view of the barrel 322 taken at line 14C-14C shown in FIG. 14A. FIG. 14D is a cross-sectional view of the barrel 322 taken at line 14D-14D shown in FIG. 14A. FIG. 15 is a cross-sectional view of the barrel 322 taken at line 15-15 shown in FIG. 14A.

As shown in FIGS. 14A-D, barrel 322 has a depression 1496 at one end and a circular protrusion 1498 at the other end. The disposable part 112 further includes a vertical wall 1402. An axle 1400 is provided to be placed between the barrel 322 and the vertical wall 1402. One end of the axle 1400 can be accommodated in a depression 1404 made in the vertical wall 1402 and the other end of the axle 1400 can be accommodated in the depression 1496. The depressions 1404, 1496 are configured to match the shape of the respective ends of the axle 1400 to allow rotation of the barrel 322 about its longitudinal X-axis. In some embodiments, small gaps can be provided between the ends of the axle and respective depressions 1404, 1496. The gaps and are provided to allow the barrel 322 to be linearly displaced with respect to its housing and along the X-axis and Z-axis.

Referring to FIGS. 14A-B and 15, the barrel 322 is configured to include a vertical partition 1410. The partition 1410 can be configured to be situated between the upper wall 534 and lower wall 536 of the disposable part 112. The partition 1410 can be further configured to be perpendicular to the longitudinal X-axis of the barrel 322. In some embodiments, the partition 1410 has a width of more than the diameter of the barrel 322. As can be understood by one skilled in the art, other widths are possible. The partition 1410 includes opposite ends 1412, 1414. The ends 1412, 1414 are configured to be accommodated by respective pockets 1416, 1418 provided in the disposable part 112, as shown in FIG. 14D. The ends 1412, 1414 are configured to fit into the pockets 1416, 1618 so that respective gaps 1420, 1422 are formed between the ends 1412, 1414 and respective pockets 1416, 1418. The gaps 1420, 1422 are configured to allow relative linear displacement of the partition 1410 with respect to the disposable part 112.

Referring back to FIGS. 14A-B, the disposable part 112 further includes a protrusion 1498 that is configured to be received within an opening made in the partition 1410. This opening can be configured to friction fit the protrusion 1498 and at the same time enable rotation of the barrel 322 about its longitudinal X-axis as well as a linear displacement of the partition 1410 along the Z-axis. In some embodiments, a small gap 1424 may be provided between the barrel 322 and the partition 1410 to allow relative linear displacement of the barrel 322 and the partition 1410 along the X-axis.

In some embodiments, the combination of the axle 1410 and the protrusion 1498 can be configured to function as a sliding bearing to allow rotation of the barrel 32 about its longitudinal X-axis. This further allows the patient (doctor or any other medical professional) to adjust an angle at which the penetration member 668 (not shown in FIGS. 14A-15) pierces the skin and at which the cannula 666 can be subcutaneously inserted into the body of the patient.

In some embodiments, the gaps 1506, 1508, 1420, 1422 and 1424 can be configured to allow relative orthogonal displacement of the barrel 322 in a horizontal plane. This can compensate for the cannula 666 being insensitive to inevitable movements of the housing when the patient wears the patch unit on his or her body. In some embodiments, the fluid delivery device 100 can include a sealing ring 1426 that is configured to provide seal between the delivery tube 120 and the disposable part 112.

Figure 16:
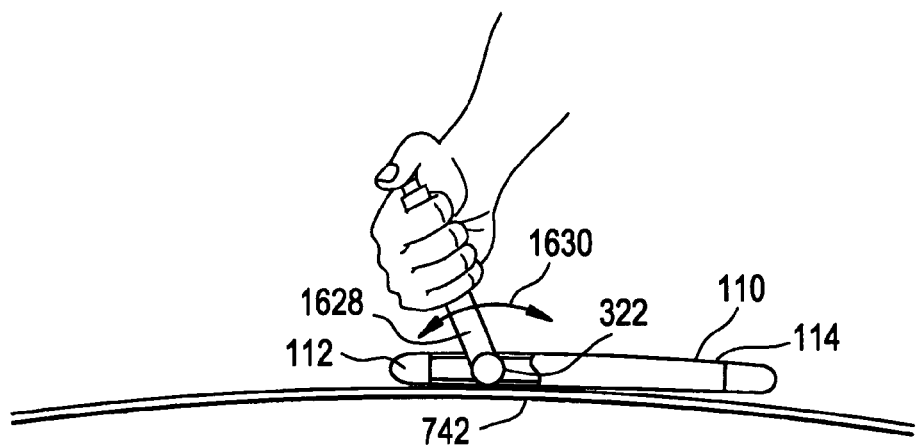
FIG. 16 illustrates an exemplary fluid delivery device configured to allow forcible rotation of the barrel, according to some embodiments of the present invention.
Figure 17:
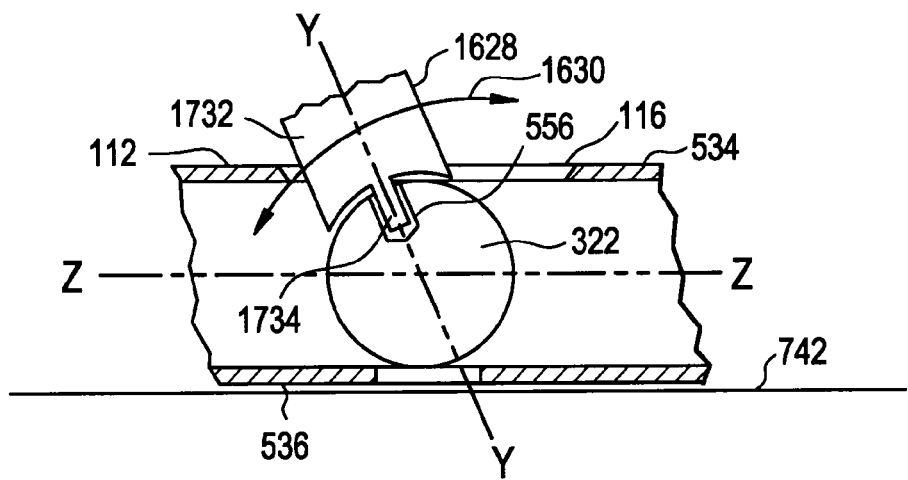
FIG. 17 is another illustration of the exemplary fluid delivery device shown in FIG. 16.
Figure 18:
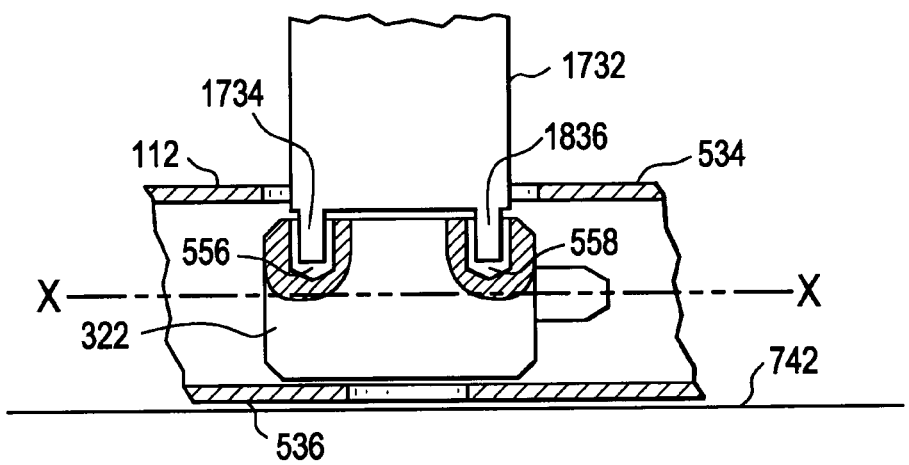
FIG. 18 is yet another illustration of the exemplary fluid delivery device shown in FIG. 16.

FIGS. 16-18 illustrate an exemplary embodiment of the fluid delivery device that is configured to allow forcible rotation of the barrel 322, according to the present invention. In some embodiments, to rotate the barrel 322, a dedicated tilting tool 1628 is used. The tool 1628 is configured to engage the barrel 322, as illustrated in FIG. 16. As shown in FIG. 16, the dedicated tilting tool 1628 can be configured as a handle and can engage the barrel through the upper aperture 116 (shown in FIG. 17). In such an embodiment, the tool 1628 can be gripped by the patient (doctor or any other medical professional) and forcibly rotated along arrow 1630 to a desirable angle. The desired angle is determines the angle at which the penetrating cartridge 662 will pierce the skin of the patient.

Referring to FIG. 17, the tilting tool 1628 includes a lower end 1732 that can be configured to include protrusions 1734 (shown in FIG. 17) and 1836 (shown in FIG. 18). The protrusions 1734 and 1836 are configured to extend away from the bottom surface of the lower end 1732. The protrusions 1734 and 1836 are configured to provide reliable engagement of the tilting tool 1628 with the barrel 322. In some embodiments, the bottom surface of the lower end 1732 is configured to match the shape of the top surface of the barrel 322. The protrusions 1734, 1836 are configured to fit into grooves 556, 558 (previously shown in FIG. 5), respectively. Thus, to adjust the angle of the barrel 322, the patient (doctor or other medical professional) inserts the tool 1628 through the aperture 116, mates the protrusions 1734, 1836 with respective grooves 556, 558 and once the tool 1628 is engaged with the barrel 322, the patient (doctor or other medical professional) rotates the barrel to the desired angle. After adjusting the barrel 322 to the desired penetration angle, the tool 1628 is removed and the penetration cartridge 662 is inserted (as discussed above with regard to FIGS. 1-13). As can be understood by one skilled in the art, insertion, rotation, and removal of the tool 1628 as well as insertion and removal of the penetration cartridge 662 can be done manually or automatically and it can further be performed by the patient, doctor, other medical professional, or any other qualified individual.

FIG. 19-23 illustrate an exemplary embodiment of a fluid delivery device that allows forcible rotation of the barrel 322 and automatic insertion of the penetration cartridge 662 into the barrel 322, according to the present invention. As shown in FIGS. 19-23, an "inserter" tool 1915 that includes the penetrating cartridge 662 inside it can be configured to provide forcible rotation of the barrel 322 and the automatic insertion of the penetration cartridge 662. In some embodiments, the inserter tool 1915 is configured to be engaged with the barrel 322 in a similar fashion discussed above with regard to FIGS. 16-18.

Figure 19:
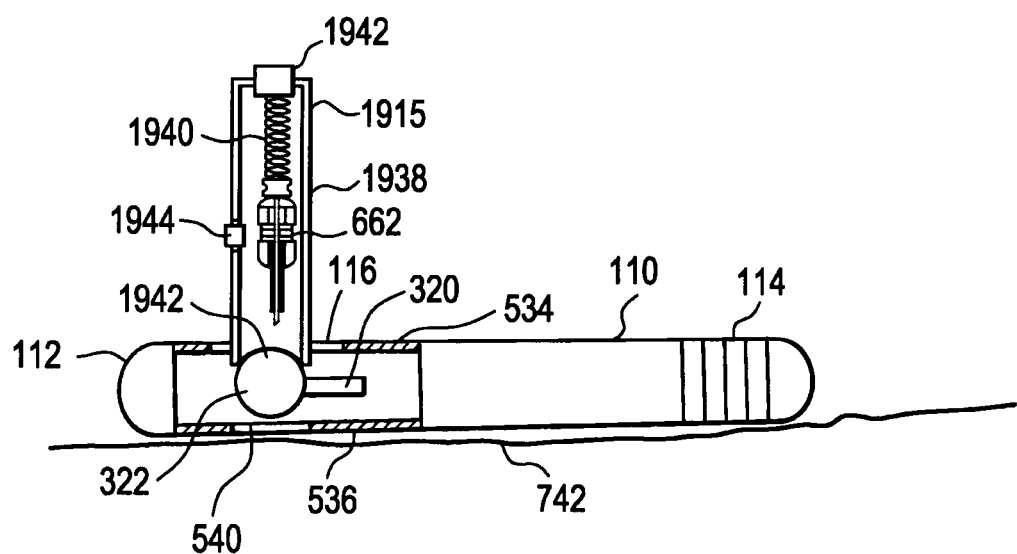
FIG. 19 illustrates an exemplary fluid delivery device configured to allow automatic insertion of the penetrating member into the barrel of the well-arrangement mechanism, according to some embodiments of the present invention.
Figure 20:
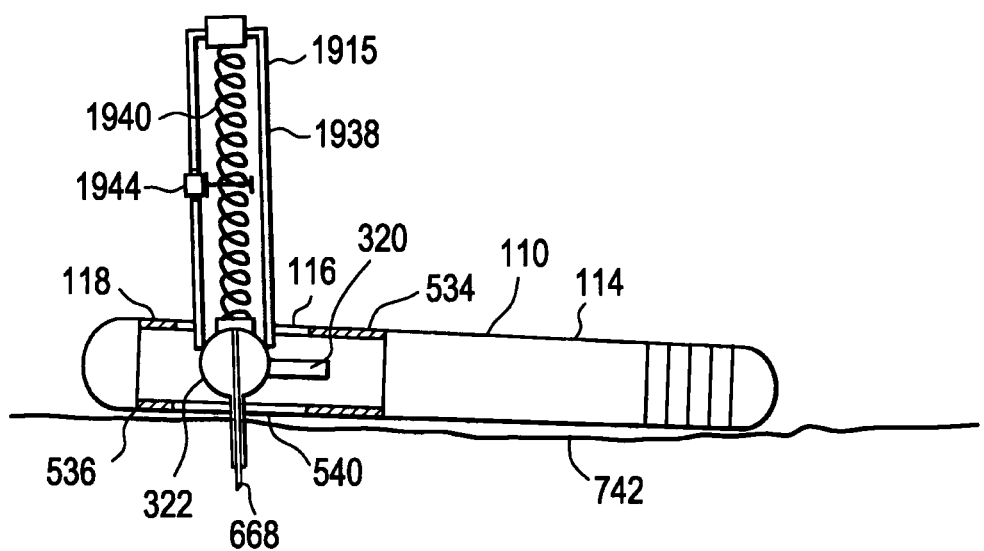
FIG. 20 is another illustration of the exemplary fluid delivery device shown in FIG. 19.

The inserter tool 1915 includes a tubular housing 1938. The patient (doctor or any other qualified individual) can grip the tubular housing for the purposes of engaging the inserter tool 1915 with the barrel 322. The interior of the tubular housing 1938 can be configured to contain the penetrating cartridge 662 and allow the penetrating cartridge 662 to slide inside the tubular housing 1938. In some embodiments, the tubular housing 1938 can also include an actuating spring 1940 and a trigger-type actuator 1942. The trigger type actuator 1942 is configured to be located at the top of the tubular housing 1938. Upon releasing the trigger-type actuator 1942, the spring 1940 is configured to displace the penetrating cartridge 662 along the length of the tubular housing 1938 between advanced and retracted positions. The advanced position is defined by the penetrating cartridge 662 being released from the tubular housing 1938 into the barrel 322 (as illustrated in FIG. 20). The retracted position is defined by the penetrating cartridge 662 being secured within the tubular housing 1938 (as illustrated in FIG. 19). As can be understood by one skilled in the art, the spring 1940 can be a coil spring, a spiral spring, or any other device that is capable of releasing the penetrating cartridge 662 into the barrel 322.

As stated above, FIG. 19 illustrates a situation when the inserter 1915 is pre-loaded with the penetrating cartridge 662 inside its housing 1938 and the actuating spring 1940 is biased so that the penetrating cartridge 662 is in its retracted position above the barrel 322. In some embodiments, prior to the delivery of therapeutic fluid to the patient, the patch unit 110 is adhered to the skin 742 of the patient and a lower end 1942 of the "inserter" tool 1915 is engaged with the barrel 322 (similar to the way discussed in FIGS. 16-18. As can be understood by one skilled in the art, other types of engaging the tool with the barrel 322 are possible). As shown in FIG. 19, the inserter tool 1915 is not yet tilted and, as such, the barrel 322 has not been forcibly rotated by the tool 1915. In some embodiments, an initial angle (prior to rotation) at which the tool 1915 is engaged with the barrel 322 is approximately 90 degrees with the regard to the top surface of the patch unit 110 (or the skin 742, or any other surface). As can be understood by one skilled in the art, other angles of engaging the tool 1915 with the barrel 322 are possible. The inserter tool 1915 can also include a safety lock mechanism 1944 that can be configured to retain the penetrating cartridge 662 in the retracted position inside the housing 1938 of the tool 1915. Once the actuator 1942 is released and the safety lock mechanism 1944 is disengaged, the penetrating cartridge 662 is released and is advanced by the spring 1940 into the barrel 322 and pierces the skin 742 of the patient using the penetration member 668 (as shown in FIG. 20).

Figure 21:
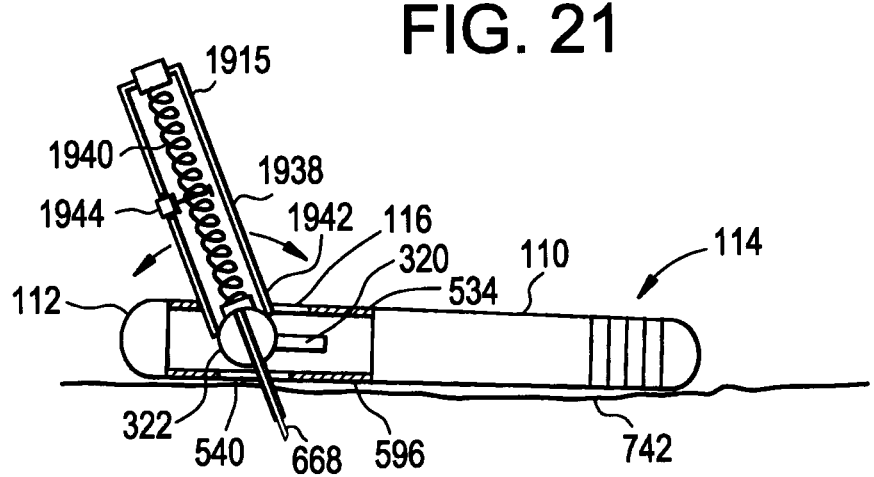
FIG. 21 illustrates an exemplary fluid delivery device configured to allow automatic insertion of the penetrating member into the barrel of the well-arrangement mechanism at a desired angle, according to some embodiments of the present invention.

FIG. 21 illustrates a situation, where the inserter tool 1915 was tilted (similarly to the way discussed in FIGS. 16-18) to a desired angle. Once the inserter tool 1915 is tilted, the penetrating cartridge 662 is released in the similar fashion shown in FIG. 19-20.

Figure 22:
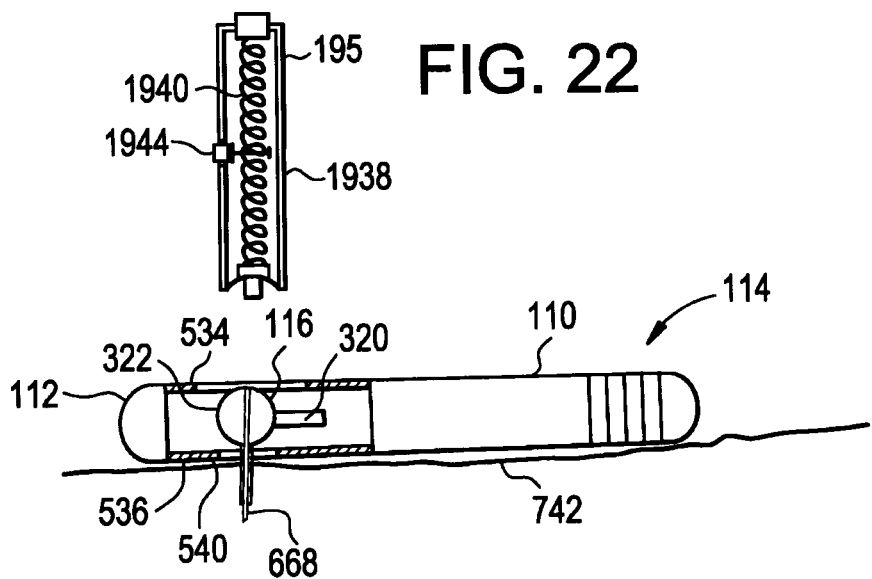
FIG. 22 illustrates the exemplary fluid delivery device shown in FIG. 19 and having a device for insertion of the penetrating cartridge removed from the barrel of the well-arrangement mechanism, according to some embodiments of the present invention.
Figure 23:
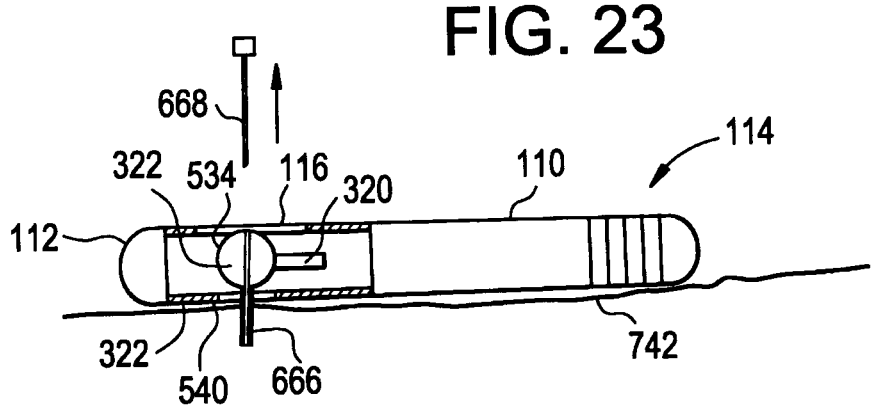
FIG. 23 illustrates an exemplary fluid delivery device having the penetrating member removed from the penetrating cartridge of the well-arrangement mechanism, according to some embodiments of the present invention.

FIGS. 22-23 illustrate the inserter tool 1915 being removed (or disengaged) from the barrel 322 and the patch unit 110. In some embodiments, the tool 1915 can be configured to be removed once the penetrating cartridge 662 has been inserted into barrel 322 and the penetrating cartridge 668 has pierced the skin 742 of the patient and the cannula 666 has been inserted in the body of the patient (as shown in FIG. 22). Once the tool 1915 is removed, the penetrating member 668 can be removed from the penetrating cartridge 662 without removing the cannula 666 (as shown in FIG. 23). As can be understood by one skilled in the art, the cannula 666 can be configured to be inserted at any desired angle. Therapeutic fluid is then subcutaneously supplied to the body of the patient via the cannula 666 that is in fluid communication with the delivery tube 320 through barrel 322.

As can be understood by one skilled in the art, the inserter tool 1915, the penetration cartridge 662, the penetration member 668 can be configured to be removed manually or automatically. In some embodiments, a spring may be provided to allow disengagement of the tool 1915 from the barrel 322.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A fluid delivery device for delivering fluid to the body of the patient, comprising:
   a housing having an upper wall and a lower wall defining an opening;
   a well-arrangement mechanism configured to be disposed inside said housing and between said upper wall and said lower wall and including a tubular member having a bore, wherein said bore is configured to be disposed within said opening;
   a penetrating cartridge for delivery of a therapeutic fluid to the body of the patient, wherein said penetrating cartridge is configured to engage said bore following its insertion through said opening; and
   a tilting tool configured to rotate said bore prior to insertion of said penetrating cartridge into said bore;
   wherein the device is configured to deliver the therapeutic fluid through said tubular member into said penetrating cartridge and into the body of the patient when said penetrating cartridge engages said bore.

2. The fluid delivery device according to claim 1, further comprising:
   a disposable part configured to include: a reservoir containing therapeutic fluid; and a delivery tube coupled to said reservoir, wherein said delivery tube is configured to be coupled to said tubular member of said well arrangement mechanism; and
   a pump configured to pump therapeutic fluid from said reservoir into said delivery tube.

3. The fluid delivery device according to claim 2, wherein said disposable part further includes said well-arrangement mechanism.

4. The fluid delivery device according to claim 2, wherein at least a portion of said disposable part is manufactured from plastic.

5. The fluid delivery device according to claim 1, wherein said tubular member includes a lateral channel configured to provide delivery of therapeutic fluid to said bore of said tubular member.

6. The fluid delivery device according to claim 1, wherein said tubular member is configured to rotate about at least one axis.

7. The fluid delivery device according to claim 1, wherein said bore is configured to rotate about at least one axis.

8. The fluid delivery device according to claim 1, wherein the penetrating cartridge further comprises:
a body portion having: a long lumen configured to extend longitudinally along said body portion; at least one short lumen configured to extend transversely across said body portion and configured to be in fluid communication with said long lumen; wherein said long lumen and said short lumen are further configured to be in fluid communication with said tubular member of said well-arrangement mechanism when said penetrating cartridge is inserted into said bore;
a cannula configured to be connected to said body portion;
a penetrating member configured to be inserted into said long lumen and said cannula, wherein said penetrating member is further configured to pierce the skin of the patient.

9. The fluid delivery device according to claim 8, wherein said penetrating member is configured to be removable from said cannula.

10. The fluid delivery device according to claim 8, wherein said long lumen and said short lumen are configured to be substantially perpendicular to each other.

11. The fluid delivery device according to claim 8, wherein said long lumen includes a sealing plug, said penetrating member is configured to pierce said sealing plug when said penetrating member is inserted into said long lumen; and wherein said sealing plug is configured to seal said long lumen when said penetrating member is inserted into said long lumen.

12. The fluid delivery device according to claim 8, wherein said penetrating member includes a needle configured to pierce the skin of the patient.

13. The fluid delivery device according to claim 8, wherein said penetrating cartridge is configured to be inserted into said bore at an angle.

14. The fluid delivery device according to claim 13, wherein said cannula is configured to deliver therapeutic fluid to the body of the patient at said angle.

15. The fluid delivery device according to claim 8, wherein said opening is configured to accommodate rotational motion of said bore and said penetrating cartridge when said penetrating cartridge is inserted into said bore.

16. The fluid delivery device according to claim 1, wherein said penetrating cartridge is configured to be manually inserted into said bore.

17. The fluid delivery device according to claim 1, wherein said penetrating cartridge is configured to be automatically inserted into said bore.

18. The fluid delivery device according to claim 1, wherein the fluid delivery device is configured as a patch unit.

19. The fluid delivery device according to claim 1, wherein therapeutic fluid is delivered subcutaneously.

20. The fluid delivery device according to claim 1, wherein therapeutic fluid is insulin.

21. The fluid delivery device according to claim 1, further comprising: a patch unit including a disposable portion and a reusable portion; wherein said disposable portion includes said well-arrangement mechanism.

22. The fluid delivery device according to claim 21, wherein said tubular member is configured to rotate such that said bore can be positioned in a plurality of positions relative to said upper wall and/or said lower wall.

23. The fluid delivery device according to claim 22, wherein the penetrating cartridge includes a body portion, a cannula and a penetrating member configured to pierce the skin of the patient, and wherein said body portion includes a first lumen for receiving fluid, and a second lumen in communication with said cannula and said first lumen.

24. A fluid delivery device for delivering fluid to the body of the patient, comprising:
a housing having an upper wall and a lower wall defining an opening;
a well-arrangement mechanism configured to be disposed inside said housing and between said upper wall and said lower wall and including a tubular member having a bore, wherein said bore is configured to be disposed within said opening;
a penetrating cartridge for delivery of a therapeutic fluid to the body of the patient, wherein said penetrating cartridge is configured to engage said bore following its insertion through said opening; and
an inserter tool configured to secure said penetrating cartridge inside a housing of said inserter tool, wherein said inserter tool is configured to rotate said bore prior to insertion of said penetrating cartridge into said bore; and upon said bore being rotated to a desired angle, said inserter tool is configured to insert said penetrating cartridge into said bore;
wherein device is configured to deliver the therapeutic fluid through said tubular member into said penetrating cartridge and into the body of the patient when said penetrating cartridge engages said bore.

25. The fluid delivery device according to claim 24, wherein said inserter tool is configured to insert said penetrating cartridge into said bore manually.

26. The fluid delivery device according to claim 24, wherein said inserter tool is configured to insert said penetrating cartridge into said bore automatically.

27. A method for delivery fluid to the body of the patient using a fluid delivery device having: a housing having an upper wall and a lower wall defining an opening; a well-arrangement mechanism configured to be disposed inside the housing and between the upper wall and the lower wall and including a tubular member having a bore, wherein the bore is configured to be disposed said opening; a penetrating cartridge for delivery of a therapeutic fluid to the body of the patient, wherein the penetrating cartridge is configured to engage the bore following its insertion through said opening; the method comprising the steps of:
rotating the bore of the well-arrangement mechanism to a desired angle using a tilting tool configured to rotate the bore prior to insertion of the penetrating cartridge into the bore;
inserting the penetrating cartridge into the bore of the well-arrangement mechanism at the desired angle until the penetrating cartridge engages the bore; and
delivering therapeutic fluid through the tubular member into the penetrating cartridge into the body of the patient.

28. The method according to claim 27, wherein said inserting step further comprises piercing the skin of the patient.

* * * * *

UNITED STATES PATENT AND TRADEMARK OFFICE
CERTIFICATE OF CORRECTION

| | |
|---|---|
| PATENT NO. | : 8,435,211 B2 |
| APPLICATION NO. | : 11/989681 |
| DATED | : May 7, 2013 |
| INVENTOR(S) | : Yodfat et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 994 days.

Signed and Sealed this
Sixth Day of January, 2015

Michelle K. Lee
*Deputy Director of the United States Patent and Trademark Office*